US007955624B2

(12) United States Patent
Heuer et al.

(10) Patent No.: US 7,955,624 B2
(45) Date of Patent: Jun. 7, 2011

(54) COMPOSITIONS AND METHODS FOR INCREASING ADIPOSE METABOLISM, LIPOLYSIS OR LIPOLYTIC METABOLISM VIA THERMOGENESIS

(75) Inventors: Marvin A. Heuer, Oakville (CA); Ken Clement, Oakville (CA)

(73) Assignee: HHC Formulations Ltd., Oakville (CA)

( * ) Notice: Subject to any disclaimer, the term of this patent is extended or adjusted under 35 U.S.C. 154(b) by 0 days.

(21) Appl. No.: 11/985,609

(22) Filed: Nov. 14, 2007

(65) Prior Publication Data
US 2008/0152732 A1 Jun. 26, 2008

Related U.S. Application Data

(62) Division of application No. 11/715,992, filed on Mar. 8, 2007.

(60) Provisional application No. 60/780,741, filed on Mar. 8, 2006.

(51) Int. Cl.
| A61K 36/00 | (2006.01) |
| A61K 36/754 | (2006.01) |
| A61K 31/4745 | (2006.01) |
| A61K 36/234 | (2006.01) |
| A61K 36/344 | (2006.01) |
| A61K 31/455 | (2006.01) |
| A61K 36/76 | (2006.01) |
| A61K 36/82 | (2006.01) |
| A61K 36/67 | (2006.01) |
| A61K 36/48 | (2006.01) |

(52) U.S. Cl. ........ 424/725; 424/729; 424/734; 424/757; 514/909

(58) Field of Classification Search .................. None
See application file for complete search history.

(56) References Cited

U.S. PATENT DOCUMENTS

| 5,998,421 | A * | 12/1999 | Yokoo et al. ................... 514/257 |
| 6,605,296 | B1 | 8/2003 | Stuckler |
| 7,595,080 | B2 | 9/2009 | Kwon |
| 2005/0074767 | A1 | 4/2005 | Lewin et al. |
| 2005/0245434 | A1* | 11/2005 | Ghosal ............................... 514/7 |
| 2006/0013903 | A1* | 1/2006 | Romero et al. ............... 424/739 |
| 2010/0099698 | A1 | 4/2010 | Park et al. |

FOREIGN PATENT DOCUMENTS
CN 1568731 A * 1/2005

OTHER PUBLICATIONS

Candiloros et al, The visceral fat reduction during weight loss with diet is proportionally higher than the body fat reduction, International journal of obesity, 2001, 25 (supplement 2): S126.*
McCarty, Pre-exercise administration of yohimbine may enhance the efficacy of exercise training as a fat loss strategy by boosting lipolysis, Medical Hypotheses, (Jun. 2002) vol. 58, No. 6, pp. 491-495.*
Badmaev et al, Diterpene forskolin (Coleus forskohlii, Benth.): a possible new compound for reduction of body weight by increasing lean body mass, NutraCos, (2002) vol. 1, No. 2, pp. 6-7.*
Anderssonet al. Systemic nicotine stimulates human adipose tissue lipolysis through local cholinergic and catecholaminergic receptors. Int J Obes Relat Metab Disord. Aug. 2001;25(8):1225-32.
Andriamampandry et al., Conversion of ethanolamine, monomethylethanolamine and dimethylethanolamine to choline-containing compounds by neurons in culture and by the rat brain. Biochem J. Dec. 1, 1989;264(2):555-62.
Barker et al., Phosphorylated inositol compounds in beta -cell stimulus-response coupling. Am J Physiol Endocrinol Metab. Dec. 2002;283(6):E1113-22.
Benzie et al., Consumption of green tea causes rapid increase in plasma antioxidant power in humans. Nutr Cancer, 1999. 34(1):83-7).
Berlan et al., Plasma catecholamine levels and lipid mobilization induced by Yohimbine in obese and non-obese women. Int J Obes. May 1991;15(5):305-15.
Bieron et al., Thrombolytic and antiplatelet action of xanthinol nicotinate (Sadamin): possible mechanisms. J Physiol Pharmacol. Jun. 1998;49(2):241-9.
Billes et al., Inhibition of Dopamine and Norepinephrine Reuptake Produces Additive Effects on Energy Balance in Lean and Obese Mice. Neuropsychopharmacology. Jul. 12, 2006.
Chidambara et al., Antioxidant and antimicrobial activity of *Cissus quadrangularis* L. J Med Food, 2003. 6(2):99-105.
Curioni et al., Weight reduction for primary prevention of stroke in adults with overweight or obesity. Cochrane Database Syst Rev. Oct. 18, 2006;(4):CD006062.
Currie et all., Yohimbine attenuates clonidine-induced feeding and macronutrient selection in genetically obese (ob/ob) mice. Pharmacol Biochem Behav. Dec. 1992;43(4):1039-46.
Del Rio et al., Cholinergic enhancement by pyridostigmine increases the insulin response to glucose load in obese patients but not in normal subjects. Int J Obes Relat Metab Disord. Dec. 1997;21(12):1111-4.
Di Marco et al., receptor-mediated regulation of cholinergic neurotransmitter phenotype in cells of central nervous system origin. Eur J Biochem. May 2000;267(10):2939-44.
Doherty et al., Effects of caffeine ingestion on exercise testing: a meta-analysis. Int J Sport Nutr Exerc Metab, 2004. 14(6):626-46.
Dulloo et al., Efficacy of a green tea extract rich in catechin polyphenols and caffeine in increasing 24-h energy expenditure and fat oxidation in humans. Am J Clin Nutr 1999;70:1040-1045).
Furukawa et al., Increased oxidative stress in obesity and its impact on metabolic syndrome. J Clin Invest. Dec. 2004;114(12):1752-61).
Galitzky et al., Alpha 2-antagonist compounds and lipid mobilization: evidence for a lipid mobilizing effect of oral Yohimbine in healthy male volunteers.*Eur J Clin Invest.* Dec. 1988;18(6):587-94.

(Continued)

*Primary Examiner* — Qiuwen Mi

(57) ABSTRACT

A composition and method for promoting weight loss through the mutual and simultaneously to promotion lipolysis, the expenditure of energy stored in the body as fat, the inhibition of lipolysis as well as affording the body of an individual protection from reactive oxygen species resulting from the β-oxidation of fats. The composition comprises at least a lipolytic substance, a thermogenic substance, a substance to inhibit the reformation of triglycerides in the bodily tissues of an individual and an antioxidant.

11 Claims, No Drawings

OTHER PUBLICATIONS

Gulcin et al., "The antioxidant and radical scavenging activities of black pepper", Int. J. of Food Sciences and Nutrition, 56:491-499, 2005.

Jainu et al., Protective effect of *Cissus quadrangularis* on neutrophil mediated tissue injury induced by aspirin in rats. J Ethnopharmacol, 2006. 104(3):302-5.

Jung et al., Antihyperglycemic activity of herb extracts on streptozotocin-induced diabetic rats. Biosci Biotechnol Biochem. Oct. 2006;70(10):2556-9.

Koba et al., Effect of phytate in soy protein on the serum and liver cholesterol levels and liver fatty acid profile in rats. Biosci Biotechnol Biochem. Jan. 2003;67(1):15-22.

Kobayashi et al., Capsaicin-like anti-obese activities of evodiamine from fruits of *Evodia rutaecarpa*, a vanilloid receptor agonist. Planta Med. Oct. 2001;67(7):628-33 Abstract.

Kucio et al., Does Yohimbine act as a slimming drug? Isr J Med Sci 1991; 27:550-556.

Loriaux et al., The effects of nicotinic acid and xanthinol nicotinate on human memory in different categories of age. A double blind study. Psychopharmacology (Berl). 1985;87(4):390-5.

Maurya et al., Radioprotection of normal tissues in tumor-bearing mice by troxerutin. J Radiat Res (Tokyo). Jun. 2004;45(2):221-8.

McCarty et al., "Pre exercise administration of yohimbine may enhance the efficacy of exercise training as a fat loss strategy by boosting lipolysis", Medical Hypothese 2002, 58:491-5.

Murthy et al., "Antioxidant and antimicrobial activity of *Cissus quandrangularis*", J. of Med. Food, 2003, 6:99-105.

Myers et al., Control of body temperature in the unanaesthetized monkey by cholinergic and aminergic systems in the hypothalamus. J Physiol. Jun. 1969;202(2):483-500.

Nagao et al., Ingestion of a tea rich in catechins leads to a reduction in body fat and malondialdehyde-modified LDL in men. Am J Clin Nutr 2005;81:122-129.

Oben et al., The effect of an extract of *Cissus quadrangularis* (Cylaris™) on weight and serum lipids in obese patients in Cameroon: a randomized double-blind clinical trial. Presented at Paris Anti-Obesity Therapies. May 2006.

Onomi et al., Effect of dietary level of phytic acid on hepatic and serum lipid status in rats fed a high-sucrose diet. Biosci Biotechnol Biochem. Jun. 2004;68(6):1379-81.

Ramkumar et al., Multiple components of the A1 adenosine receptor-adenylate cyclase system are regulated in rat cerebral cortex by chronic caffeine ingestion. J Clin Invest. 1988, 82(1):242-7.

Raza et al., "Green tea polyphenol epigallocatechin-3-gallate differentially modulates oxidative stress in PC12 cell compartments", Toxicology and Appl. Pharm., 2005, 207:212-220.

Squires et al., Low-dose, time-release nicotinic acid: effects in selected patients with low concentrations of high-density lipoprotein cholesterol. *Mayo Clin Proc.* Sep. 1992; 67(9):855-60.

Vucenik et al., Cancer inhibition by inositol hexaphosphate (IP6) and inositol: from laboratory to clinic. J Nutr. Nov. 2003;133(11 Suppl 1):3778S-3784S.

Westerterp KR. Diet induced thermogenesis. Nutr Metab (Lond). Aug. 18, 2004;1(1):5.

Yoshida et al., Relationship between basal metabolic rate, thermogenic response to caffeine, and body weight loss following combined low calorie and exercise treatment in obese women. Int J Obes Relat Metab Disord, 1994. 18(5):345-50.

Adam et al., Troxerutin protects the isolated perfused rat liver from a possible lipid peroxidation by coumarin. Phytomedicine. Jan. 2005;12(1-2):52-61.

Chung et al., Efficacy of troxerutin on streptozotocin-induced rat model in the early stage of diabetic retinopathy. Arzneimittelforschung. 2005;55(10):573-80.

Haubrich et al., Deanol affects choline metabolism in peripheral tissues of mice. J Neurochem. Aug. 1981;37(2):476-82.

Kobayashi et al., Capsaicin-like anti-obese activities of evodiamine from fruits of *Evodia rutaecarpa*, a vanilloid receptor agonist. Planta Med. Oct. 2001;67(7):628-33.

Lee et al., Inhibition of diacylglycerol acyltransferase by alkamides isolated from the fruits of *Piper longum* and *Piper nigrum*. J Agric Food Chem. Dec. 27, 2006;54(26):9759-63.

Yoshizumi et al., Effect of evodiamine on catecholamine secretion from bovine adrenal medulla. J Med Invest. Aug. 1997;44(1-2):79-82.

Archimowicz-Cyrylowska et al. Clinical Effect of Buckwheat Herb, Ruscus Extract and Troxerutin on Retinopathy and Lipids in Diabetic Patients. Phytotherapy Research. vol. 10 Issue 8, pp. 659-662. 1996.

Coon and Ernst; Complementary and alternative therapies in the treatment of chronic hepatitis C: a systematic review J. Hematology 40:491-500 (2004).

\* cited by examiner

COMPOSITIONS AND METHODS FOR INCREASING ADIPOSE METABOLISM, LIPOLYSIS OR LIPOLYTIC METABOLISM VIA THERMOGENESIS

RELATED APPLICATIONS

This application is a divisional of and claims the benefit of priority to U.S. application Ser. No. 11/715,992, filed Mar. 8, 2007, which is hereby incorporated by reference in its entirety, which in turn is related to and claims the benefit of priority to the Applicant's U.S. Provisional Patent Application No. 60/780,741 entitled "Compositions and Methods for Increasing Adipose Metabolism or Lipolysis or Lipolytic Metabolism via Thermogenesis" filed Mar. 8, 2006, the disclosure of which is hereby fully incorporated by reference.

FIELD OF THE INVENTION

The present invention is related to compositions and methods for increasing an individual's natural ability to utilize adipose tissue as an energy source via adipose metabolism. Specifically, the adipose metabolism occurs through mechanisms of lipolysis or lipolytic metabolism for the purposes of reducing body fat mass and fat loss.

SUMMARY OF THE INVENTION

The present invention is directed towards a diet supplement comprising a lipolytic substance, a thermogenic substance, a substance to inhibit the reformation of triglycerides in the bodily tissues of an individual and an antioxidant. The ingredients of the present composition act to mutually and simultaneously promote lipolysis, the expenditure of energy stored in the body as fat, inhibits lipolysis and affords the body of an individual protection from reactive oxygen species resulting from the β-oxidation of fats. A method of providing same is also provided.

BACKGROUND

Obesity has become an increasingly widespread and predominant health concern. According to the World Health Organization (WHO) obesity is considered a multifactorial chronic disease which is increasing in frequency (Curioni C, Andre C, Veras R. Weight reduction for primary prevention of stroke in adults with overweight or obesity. Cochrane Database Syst Rev. 2006 Oct. 18; (4):CD006062). Obesity, a condition of excessive body fat, generally results from more energy (food) being consumed than is being used. Stemming from excessive body fat, several health-related concerns such as increased morbidity have linked to obesity and being overweight as well as hypertension, coronary heart disease, type 2 diabetes mellitus, stroke and even some forms of cancer (Curioni C, Andre C, Veras R. Weight reduction for primary prevention of stroke in adults with overweight or obesity. Cochrane Database Syst Rev. 2006 Oct. 18; (4):CD006062).

One of the main contributing factors in obesity is overeating, which results in an excess of energy being consumed in relation to the amount of being energy expended by an individual. The excess energy is then stored largely as fat. A simplified determination of an individual's body weight is essentially governed by the net effect of energy consumed versus energy expended. Daily energy expenditure consists of three components: basal metabolic rate, adaptive thermogenesis and physical activity (Westerterp K R. Diet induced thermogenesis. Nutr Metab (Lond). 2004 Aug. 18; 1(1):5).

All of the aforementioned components must be in a balance of energy expenditure in an individual with energy or food intake such an individual does not gain nor lose body weight fat adipose issue reduction. Therefore, in order that person may lose body weight from a reduction in adipose tissue, more energy must be expended by the individual than in taken into the body.

An undesired effect of increased accumulation of body fat is an increased oxidative stress through the generation of reactive oxygen species and the downregulation of antioxidative enzymes. This downregulation of antioxidative enzymes can contribute to the pathogenesis of diabetes, hypertension and atherosclerosis (Furukawa S, Fujita T, Shimabukuro M, Iwaki M, Yamada Y, Nakajima Y, Nakayama O, Makishima M, Matsuda M, Shimomura I. Increased oxidative stress in obesity and its impact on metabolic syndrome. J Clin Invest. 2004 December; 114(12):1752-61). Thus it is desirable to provide to the body of an individual means to reduce stored body fat and simultaneously offer protection from reactive oxygen species. It is likely that the oxidative stress associated with obesity involves mechanisms distinct from those solely due to mitochondrial beta-oxidation of fats. Increased oxidative stress due to increased body fat is thought to be an early contributor to hypertension, coronary heart disease, type 2 diabetes mellitus, stroke and even some forms of cancer and is therefore an attractive target strategy for combating the negative effects of excessive body fat while aiming to reduce the volume of stored body in an individual.

With the unprecedented rise in obesity throughout the world, here exists both a need and want from individuals for improved aids, methods and interventions directed to reducing body fat and maintaining lowered levels of body fat, while also supplying beneficial antioxidant activity.

DETAILED DESCRIPTION OF THE INVENTION

In the following description, for the purposes of explanations, numerous specific details are set forth in order to provide a thorough understanding of the present invention. It will be apparent, however, to one skilled in the art that the present invention may be practiced without these specific details.

The present invention, according to various embodiments thereof, provides a composition and method for increasing an individual's natural adipose metabolism occurring through mechanisms of lipolysis or lipolytic metabolism, thermogenesis and inhibition of the reformation of triglycerides for the purposes of reducing body fat mass and fat loss. In addition, in various embodiments, simultaneous means of affording protection to the body of individual from reactive oxygen species resulting from the β-oxidation of fats is also provided by way of a compositions and methods. Preferably, the composition is that of a dietary supplement.

According to various embodiments of the present invention, compositions are provided which facilitate in the reduction of body fat mass, leading to fat loss; simultaneously affording protection to the body of an individual from reactive oxygen species resulting from the β-oxidation of fats.

DEFINITIONS

The term 'fat' as used herein is understood to represent lipids and includes related forms such as triglycerides, cholesterol, high density lipoproteins (HDL), low density lipoproteins (LDL) and fatty acids.

Furthermore, as herein in the present disclosure, it is understood that cells that store fat are termed 'adipocytes' and that adipose tissue is comprised of adipocytes.

The term 'adipocyte metabolism' as used herein is understood to represent any biological process which causes or leads to an impact on fat and includes but is not limited to anabolism or synthesis, catabolism or breakdown, degradation, lipolysis and forms of oxidation.

Although not wishing to be bound by theory, in the present invention, free-circulating norepinephrine is understood to be responsible for the stimulation of β-receptors on the cell surface of adipose cells. The stimulation of β-receptors via norepinephrine using cyclic adenosine monophosphate (cAMP) as a second messenger stimulates the release of fatty acids from adipose cells The released fatty acids then undergo a thermogenic metabolic process whereby the fat is converted into body heat and released.

In one aspect of the present invention the composition comprises components that have been shown to induce lipolysis in adipose tissue. It is understood that the aforementioned combination of components will have an additive effect relating to lipolysis and energy expenditure. Lipolysis has been shown to lead to a decrease in both the lipid content of individual adipocytes as well as the number of adipocytes.

In another aspect of the present invention the composition comprises components for the inhibition of phosphodiesterases. Phosphodiesterases are known to degrade intracellular cAMP. Therefore, the inhibition of phosphodiesterases allows for the continued release of fatty acids from adipose tissue and thermogenesis via a cAMP-dependant mechanism.

Another aspect of the present invention comprises components which inhibit the breakdown of the norepinephrine via the inhibition of catechol-O-methyltransferase (COMT). COMT is the enzyme responsible for the degradation of norepinephrine. Inhibition of COMT leads to an elevated level of norepinephrine.

Additionally, the present invention is designed to inhibit the stimulation of $\alpha_2$-receptors on the cell of adipose cells. When stimulated, an $\alpha_2$-receptor stops the breakdown of fat and subsequently inhibits a reduction body fat mass (Kucio C, Jonderko K, Piskorske D. Does Yohimbine act as a slimming drug? Isr J Med Sci 1991; 27:550-556). To further ensure the inhibition of stimulation of $\alpha_2$-receptors, the binding of norepinephrine to its α-receptor on nerve cell is inhibited by components of the composition. Since norepinephrine is released via a negative feedback loop, the present invention allows for the maintenance of circulating norepinephrine through the interruption of the negative feedback loop. Subjects consuming the components in a composition of the invention showed a 40% increase in norepinephrine relative to control subjects (Dulloo A G, Duret C, Rohrer D, Girardier L, Mensi N, Fathi M, Chantre P, Vandermander J. Efficacy of a green tea extract rich in catechin polyphenols and caffeine in increasing 24-h energy expenditure and fat oxidation in humans. Am J Clin Nutr 1999; 70:1040-1045). In studies on ingredients of the present invention; consumption of components in a composition of the invention in combination with an intense diet, subjects lost on average 60% more weight than the placebo group over the course of the study (Kucio C, Jonderko K, Piskorske D. Does Yohimbine act as a slimming drug? Isr J Med Sci 1991; 27:550-556). Moreover, in another study, subjects consuming the components in a composition of the invention showed a 7.9% reduction in total area of body fat as compared to control groups as determined by CT scan (Nagao T, Komine Y, Soga S, Meguro M, Hase T, Yukitaka T, Tokimitsu I. Ingestion of a tea rich in catechins leads to a reduction in body fat and malondialdehyde-modified LDL in men. Am J Clin Nutr 2005; 81:122-129).

Green Tea Extract (ECGC, Catechins and Polyphenols)

The active compounds of green tea are a family of polyphenols with tannins being the largest of the subgroups contained therein. The most active specific compound of the polyphenols is epigallocatechin gallate (ECGC) which comprises 10-50% of the total the catechins found in green ten. Furthermore, caffeine is also a major active component of green tea, however the percentage of caffeine contained in extracts of green tea fluctuates significantly owing to several different factors such as processing, for example.

Green tea principally acts in a beneficial way through the polyphenols' antioxidant activities as evidenced by several laboratory studies. One clinical study has shown that the ingestion of an extract of green tea results in a rapid increase in plasma antioxidant activity (Benzie I F, Szeto Y T, Strain J J, Tomlinson B. Consumption of green tea causes rapid increase in plasma antioxidant power in humans. Nutr Cancer, 1999. 34(1):83-7).

Moreover, green tea has also been shown to be effective in aiding weight loss. This effect may be due to two activities. Green tea both reduces fat digestion and increases energy expenditure (Berube-Parent S, Pelletier C, Dore J, Tremblay A. Effects of encapsulated green tea and Guarana extracts containing a mixture of epigallocatechin-3-gallate and caffeine on 24 h energy expenditure and fat oxidation in men. Br J Nutr, 2005, 94(3):432-6). Fat stores may provide the energy necessary for the increase in energy expenditure via the oxidation of fat, consequently leading to thermogenesis. The thermogenic activity of green tea may additionally be greatly enhanced by synergistic cooperation with additionally added caffeine. In the regard the β-oxidation of fats owing to green tea is a result of activities at adenosine receptors and their effect on and increase in cyclic adenosine monophosphate (cAMP).

Additionally, the mechanism of action of green tea may also be, at least partially, due to an increase in norepinephrine. Catechins, found in green tea, are known to inhibit catechol-O-methyl-transferase (COMT), an enzyme which degrades norepinephrine. In turn, norepinephrine inhibits the degradation of cyclic adenosine monophosphate (cAMP). Furthermore, increasing norepinephrine levels by the inhibition of norepinephrine uptake results in increased weight loss in both lean and obese mice as evidenced in animal studies (Billes S K, Cowley M A. Inhibition of Dopamine and Norepinephrine Reuptake Produces Additive Effects on Energy Balance in Lean and Obese Mice. Neuropsychopharmacology. 2006 Jul. 12). Stemming from increased norepinephrine levels is the result of an increased interaction with adrenergic receptors which are known to regulate lipolysis, again acting to further aiding in the reduction of body fat.

In an embodiment of the present invention which is set forth in greater detail in the examples below, the diet supplement includes an extract of green tea dry leaf (*Camellia sinensis*). A serving of the diet supplement includes from about 0.1 g to about 0.7 g of an extract of green tea dry leaf (*Camellia sinensis*). The preferred dosage in a serving of the diet supplement of the present invention comprises about 0.4600 g of an extract of green tea dry leaf (*Camellia sinensis*).

Anhydrous Caffeine

Caffeine is a naturally occurring xanthine alkaloid found in some plants where it serves as a natural pesticide. It is also common additive to food products, especially beverages for human consumption and as such, it has numerous beneficial effects, the most common of which uses caffeine as a supplement to the central nervous system. In this capacity, it is used as both a neuro-stimulant and performance enhancer. A meta-analysis compiled from forty double-blind studies supports the use of caffeine to increase physical endurance (Doherty M, Smith P M. Effects of caffeine ingestion on exercise testing: a meta-analysis. Int J Sport Nutr Exerc Metab, 2004. 14(6):626-46).

Caffeine is also widely used to control weight, which may occur through multiple mechanisms. Significant weight loss related to caffeine supplementation has been observed in obese women (Yoshida T, Sakane N, Umekawa T, Kondo M. Relationship between basal metabolic rate, thermogenic response to caffeine, and body weight loss following combined low calorie and exercise treatment in obese women. Int J Obes Relat Metab Disord, 1994. 18(5):345-50), which may be, at least in part, due to increased lipolysis as fat is metabolized. Caffeine has additionally been shown to increase the basal metabolic rate in humans wherein this also adds to its weight-lowering effects via increased energy expenditure.

Biochemically, caffeine, as it is structurally similar to adenosine, binds to, but does not activate, adenosine receptors which are normally activated by adenosine to induce sleep. Thus, caffeine acts as a stimulant through having the opposite effect of the receptor's natural ligand, adenosine. By antagonizing certain adenosine receptors, caffeine has the effect of increasing levels of intracellular cAMP, which is an important signaling molecule involved in many metabolic processes including thermogenesis (Ramkumar V, Bumgarner J R, Jacobson K A, Stiles G L. Multiple components of the A1 adenosine receptor-adenylate cyclase system are regulated in rat cerebral cortex by chronic caffeine ingestion. J Clin Invest. 1988, 82(1):242-7). As an additional function with respect to cAMP, caffeine also enables the increase cAMP levels through the inhibition of phosphodiesterases which specifically degrade cAMP. The ensuing actions of caffeine with respect to the cAMP system lead to an increase in the release of epinephrine and norepinephrine. Since epinephrine and norepinephrine use cAMP for signaling, increased levels of cAMP will yield increased adrenergic signaling thereby inducing lipolysis, where thermogenesis can expend energy leading to body fat loss.

In an embodiment of the present invention which is set forth in greater detail in the examples below, the diet supplement includes an effective amount of anhydrous caffeine. A serving of the diet supplement includes from about 0.1 g to about 0.5 g of anhydrous caffeine. In the preferred dosage of the present invention, a serving of the diet supplement comprises about 0.3000 g of anhydrous caffeine.

*Cissus quadrangularis* Extract (from Stem and Leaf)

*Cissus quadrangularis* is a plant indigenous to India where it is largely used in traditional medicine. Extracts of *Cissus quadrangularis* have additionally been shown to be effective as a weight loss agents. Clinical studies have shown that in a randomized double-blind trial, a group taking an extract of *Cissus quadrangularis* for 6-weeks lost more weight, had lower cholesterol, as well as reduced LDL and fasting blood glucose levels as compared to the control groups. The experimental group also displayed increased HDL levels as compared to a placebo group (Oben J E, Mandob D, Fomekong G, Momo C. The effect of an extract of *Cissus quadrangularis* (Cylaris™) on weight and serum lipids in obese patients in Cameroon: a randomized double-blind clinical trial. Presented at Paris Anti-Obesity Therapies. May 2006), suggesting an additional effect on cholesterol.

Moreover, for the purposes of the present invention, extracts of *Cissus quadrangularis* contain sterols, vitamin C, and tannins, which have antimicrobial and antioxidant activity (Chidambara Murthy K N, Vanitha A, Mahadeva Swamy M, Ravishankar G A. Antioxidant and antimicrobial activity of *Cissus quadrangularis* L, J Med Food, 2003. 6(2):99-105). The antioxidant activity of *Cissus quadrangularis* has been proposed to be one of the mechanisms by which it shows protection against tissue injury in animal models (Jainu M, Mohan K V, Devi C S. Protective effect of *Cissus quadrangularis* on neutrophil mediated tissue injury induced by aspirin in rats. J Ethnopharmacol, 2006. 104(3):302-5).

In an embodiment of the present invention which is set forth in greater detail in the examples below, the diet supplement includes an extract of *Cissus quadrangularis*. A serving of the diet supplement includes from about 0.05 g to about 0.3 g of an extract of *Cissus quadrangularis*. In the preferred dosage of the present invention, in a serving of said diet supplement comprises about 0.1500 g of *Cissus quadrangularis* extract.

*Evodia rutaecarpia* Extract

*Evodia* species of plants are a source of many chemicals with a variety of potentially beneficial actions. One specific chemical is evodiamine, which has been shown to increase the secretion of adrenergic signaling molecules and stimulate the sympathetic nervous system (Yoshizumi M, Houchi H, Ishimura Y, Hirose M, Kitagawa T, Tsuchiya K, Minakuchi K, Tamaki T. Effect of evodiamine on catecholamine secretion from bovine adrenal medulla. J Med Invest. 1997 August; 44(1-2):79-82 Abstract). Evodiamine has also been shown to increase energy expenditure and lipid mobilization and decrease body fat in mice (Kobayashi Y, Nakano Y, Kizaki M, Hoshikuma K Yokoo Y, Kamiya T. Capsaicin-like anti-obese activities of evodiamine from fruits of *Evodia rutaecarpa*, a vanilloid receptor agonist. Planta Med. 2001 October; 67(7): 628-33 Abstract), through the increase in adrenergic signaling molecule secretions.

In an embodiment of the present invention, which is set forth in greater detail in the examples below, the nutritional supplement includes *Evodia rutaecarpia* extract. A serving of the nutritional supplement includes from about 0.005 g to about 0.02 g of *Evodia rutaecarpia* extract. In the preferred dosage of the present invention, a serving of the diet supplement comprises about 0.01 g of *Evodia rutaecarpia* extract.

Deanol

Deanol is an organic compound also commonly known by the synonyms: dimethylaminoethanol, dimethylethanolamine or DMAE. Deanol is involved in synthesis of the neurotransmitter acetylcholine via involvement in choline metabolism. The cholinergic system pertains to any aspect affecting the function of acetylcholine. Furthermore, digestion and energy conservation at periods of rest are exclusively governed by acetylcholine signaling in the parasympathetic nervous system. Moreover, the cholinergic system has been implicated in several disease conditions including obesity. In an elaborate experiment by Myers and Yaksh using primates, acetylcholine was demonstrated to be involved in thermoregulation (Myers R D, Yaksh T L. Control of body temperature in the unanaesthetized monkey by cholinergic and aminergic systems in the hypothalamus. J Physiol. 1969 June; 202(2):483-500). In addition to thermoregulation, cholinergic signaling has been linked to food intake and satiety (Di Marco A, Demartis A, Gloaguen I, Lazzaro D, Delmastro P, Ciliberto G, Laufer R. Leptin receptor-mediated regulation of cholinergic neurotransmitter phenotype in cells of central nervous system origin. Eur J Biochem. 2000 May; 267(10): 2939-44) and lipolysis in human adipocytes (Andersson K, Arner P. Systemic nicotine stimulates human adipose tissue lipolysis through local cholinergic and catecholaminergic receptors. Int J Obes Relat Metab Disord. 2001 August; 25(8):1225-32). A further role cholinergic signaling may play in obesity is suggested by it's involvement in insulin secretion in obese individuals (Del Rio G, Procopio M, Bondi M, Marrama P, Menozzi R, Oleandri S E, Grottoli S, Maccario M, Velardo A, Ghigo E. Cholinergic enhancement by pyridostigmine increases the insulin response to glucose load in obese patients but not in normal subjects. Int J Obes Relat Metab Disord. 1997 December; 21(12):1111-4 Abstract).

One of the most important sources of choline is through the diet and deanol which has been shown to be capable of conversion into choline-containing compounds (Andriamampandry C, Freysz L, Kanfer J N, Dreyfus H, Massarelli R. Conversion of ethanolamine, monomethylethanolamine and dimethylethanolamine to choline-containing compounds by neurons in culture and by the rat brain. Biochem J. 1989 Dec. 1; 264(2):555-62). Treatment of mice with deanol has been shown to increase plasma and tissue levels of choline, at least in part, by inhibiting the metabolism of choline (Haubrich D R, Gerber N H, Pflueger A B. Deanol affects choline metabolism in peripheral tissues of mice. J Neurochem. 1981 August; 37(2):476-82 Abstract).

In an embodiment of the present invention which is set forth in greater detail in the examples below, the diet supplement includes deanol bitartrate. A serving of the diet supplement includes from about 0.05 g to about 0.2 g of deanol bitartrate. The present invention, in a preferred dosage of said dietary supplement comprises about 0.1 g of deanol bitartrate per serving.

Xanthinol Nicotinate

Xanthinol nicotinate is one of several forms of the vitamin Niacin (vitamin B3 or nicotinic acid). It easily passes through the cell membrane and is considered the most potent form of Niacin. Pharmaceutically, xanthinol nicotinate is classified as a vasodilator and presents in human with a "flushed" to the skin.

In patients with peripheral arterial obliterative disease, xanthinol nicotinate was found to have anti-platelet and thrombolytic actions accompanied by an increase in the release of NO (Bieron K, Swies J, Kostka-Trabka E, Gryglewski R J. Thrombolytic and antiplatelet action of xanthinol nicotinate (Sadamin): possible mechanisms. J Physiol Pharmacol. 1998 June; 49(2):241-9). Xanthinol nicotinate may also have the effects of enhancing cellular metabolism and increasing oxygen supply to tissues. This may be the mechanism by which improvements in both short- and long-term memory associated with the administration of xanthinol nicotinate three times per day for eight weeks in a double blind study (Loriaux S M, Deijen J B, Orlebeke J F, De Swart J H. The effects of nicotinic acid and xanthinol nicotinate on human memory in different categories of age. A double blind study. Psychopharmacology (Berl). 1985; 87(4):390-5) were realized.

In a comparative study of 117 individuals, 63 treated with Niacin and 54 treated with a placebo, active treatment resulted in an increase in high-density lipoprotein cholesterol (HDL-C), a decrease in total cholesterol, low-density lipoprotein cholesterol (LDL-C), and triglyceride levels (Squires R W, Allison T G, Gau G T, Miller T D, Kottke B A. Low-dose, time-release nicotinic acid: effects in selected patients with low concentrations of high-density lipoprotein cholesterol. Mayo Clin Proc. 1992 September; 67(9):855-60). Niacin achieves the aforementioned results by reducing lipoprotein synthesis in the liver.

In an embodiment of the present invention, which is set forth in greater detail in the examples below, the dietary supplement includes xanthinol nicotinate. A serving of the dietary supplement includes from about 0.02 g to about 0.1 g of xanthinol nicotinate. The preferred dosage of a serving of the dietary supplement comprises about 0.0500 g of xanthinol nicotinate or derivatives thereof.

Inositol Hexaphosphate

Inositol hexaphosphate, also commonly known as phytic acid, is the main storage form of phosphorous in cereals and legumes. Most mammalian cells contain inositol hexaphosphate which serves as an important signaling molecule involved in anti-cancer and antioxidant activities (Vucenik I, Shamsuddin A M. Cancer inhibition by inositol hexaphosphate (IP6) and inositol: from laboratory to clinic. J Nutr. 2003 November; 133(11 Suppl 1):3778S-3784S) which is understood to be related to the ability of inositol hexaphosphate to chelate metal ions that can produce free-radicals.

Dietary Inositol hexaphosphate has been shown to improve parameters of blood-lipids. Rats fed a high sucrose diet displayed a dose-dependent response to inositol hexaphosphate (0.02%, 0.1%, 0.5%, 2.5%, 5% and 10% phytic acid) in terms of reducing triglycerides, cholesterol and lipogenic enzymes (Onomi S, Okazaki Y, Katayama T. Effect of dietary level of phytic acid on hepatic and serum lipid status in rats fed a high-sucrose diet. Biosci Biotechnol Biochem. 2004 June; 68(6):1379-81). At the highest dose (10% phytic acid) there was also a reduction in food intake and growth. Similar improvements were also found with rats fed a high-cholesterol diet (Koba K, Liu J W, Bobik E Jr, Mills D E, Sugano M, Huang Y S. Effect of phytate in soy protein on the serum and liver cholesterol levels and liver fatty acid profile in rats. Biosci Biotechnol Biochem. 2003 January; 67(1):15-22). Inositol phosphate also has an effect on insulin secretion from beta-cells via the release of calcium (Barker C J, Leibiger I B, Leibiger B, Berggren P O. Phosphorylated inositol compounds in beta-cell stimulus-response coupling. Am J Physiol Endocrinol Metab. 2002 December; 283(6):E1113-22).

In an embodiment of the present invention, which is set forth in greater detail in the examples below, the dietary supplement includes inositol hexaphosphate. A serving of the dietary supplement includes from about 0.01 g to about 0.04 g of inositol hexaphosphate. The preferred dosage of a serving of the dietary supplement comprises about 0.0200 g of inositol hexaphosphate.

*Sophora japonica*

*Sophora japonica* is a small tree native to Asia that has been introduced to most parts of the world and is an ingredient in Traditional Chinese Medicine. Toxerutin is a derivative of ruin, which is a natural bioflavinoid extracted from *Sophora japonica*.

Oral administration of *Sophora japonica* to chemically-induced diabetic rats (Jung C H, Zhou S, Ding G X, Kim J H, Hong M H, Shin Y C, Kim G J, Ko S G. Antihyperglycemic activity of herb extracts on streptozotocin-induced diabetic rats. Biosci Biotechnol Biochem. 2006 October; 70(10):2556-9) and radiation-exposed rats (Maurya D K, Salvi V P, Krishnan Nair C K. Radioprotection of normal tissues in tumor-bearing mice by troxerutin. J Radiat Res (Tokyo). 2004 June; 45(2):221-8) improved measures of lipid peroxidation by reactive oxygen species and to scavenge damaging free-radicals which are known to cause complications diabetes. Indeed, toxerutin, an active antioxidant of *Sophora japonica*, has been shown to show promise as a treatment for diabetic retinopathy in rat models (Chung H K, Choi S M, Ahn B O, Kwak H H, Kim J H, Kim W B. Efficacy of troxerutin on streptozotocin-induced rat model in the early stage of diabetic retinopathy. Arzneimittelforschung. 2005; 55(10):573-80 Abstract) and as a liver protectant from lipid peroxidation (Adam B S, Pentz R, Siegers C P, Strubelt O, Tegtmeier M. Troxerutin protects the isolated perfused rat liver from a possible lipid peroxidation by coumarin. Phytomedicine. 2005 January; 12(1-2):52-61 Abstract).

In an embodiment of the present invention which is set forth in greater detail in the examples below, the diet supplement includes an extract of *Sophora japonica*. A serving of the diet supplement includes from about 0.01 g to about 0.04 g of an extract of *Sophora japonica*. The preferred dosage in a serving of said diet supplement comprises about 0.02 g of *Sophora japonica* extract Black Pepper Extract Black pepper, also known as *Piper nigrum*, is a flowering vine cultivated for its fruit which is usually dried for use as a spice and seasoning. Many of the active constituents of black pepper contribute to it's high antioxidant activity, which rivals that of potent synthetic antioxidants. Black pepper also appears to be beneficial for weight reduction through the inhibition of diacylglycerol acyltransferase (DGAT) (Lee S W, Rho M C, Park H R, Choi J H, Kang J Y, Lee J W, Kim K, Lee H S, Kim Y K. Inhibition of diacylglycerol acyltransferase by alkamides isolated from the fruits of *Piper longum* and *Piper nigrum*. J Agric Food Chem. 2006 Dec. 27; 54(26): 9759-63 Abstract), an enzyme involved in triglyceride synthesis, which provides another anti-obesity therapeutic strategy.

In an embodiment of the present invention which is set forth in greater detail in the examples below, the diet supplement includes an extract of black pepper. A serving of the diet supplement includes from about 0.001 mg to about 0.008 mg of black pepper extract. The present invention, in a preferred dosage said diet supplement comprises about 0.005 g of black pepper extract per serving.

Yohimbine Hydrochloride

Yohimbine is a naturally occurring alkaloid derived from the African tree, *Pausinysatlia yohimbe*. Furthermore, yohimbine has been shown through research to increase the amount of non-esterified fatty acids (NEFAs) in the bloodstream, as a product of lipolysis in both lean and obese individuals (Berlan M, Galitzky J, Riviere D, Foureau M, Tran M A, Flores R, Louvet J P, Houin G, Lafontan M. Plasma catecholamine levels and lipid mobilization induced by Yohimbine in obese and non-obese women. Int J, Obes. 1991 May; 15(5):305-15; Galitzky J, Taouis M, Berlan M, Riviere D, Garrigues M Lafontan M. Alpha 2-antagonist compounds and lipid mobilization: evidence for a lipid mobilizing effect of oral Yohimbine in healthy male volunteers. Eur J Clin Invest. 1988 December; 18(6):587-94.). Additionally this effect persists for upwards of 14 days, indicating that a rapid tolerance, as seen with several other known lipolytic agents, to yohimbine does not develop (Galitzky J, Taouis M, Berlan M, Riviere D, Garrigues M Lafontan M. Alpha 2-antagonist compounds and lipid mobilization: evidence for a lipid mobilizing effect of oral Yohimbine in healthy male volunteers. Eur J Clin Invest. 1988 December; 18(6):587-94.). In addition to its effects on lipolysis, Yohimbine is also an appetite suppressant, and has been shown to decrease energy intake in both lean and obese mice (Currie P J, Wilson L M. Yohimbine attenuates clonidine-induced feeding and macronutrient selection in genetically obese (ob/ob) mice. Pharmacol Biochem Behav. 1992 December; 43(4):1039-46.) Researchers also found that in a 3-week study utilizing 20-obese-female subjects wherein the subjects were restricted to a 1000 calories per day diet, that 20 mg of yohimbine administered daily increased weight loss by an additional 3 pounds over the placebo group (Kucio C, Jonderko K, Piskorska D. Does Yohimbine act as a slimming drug? Isr J Med Sci. 1991 October; 27(10):550-6.).

In an embodiment of the present invention which is set forth in greater detail in the examples below, the diet supplement includes Yohimbine HCl. A serving of the diet supplement includes from about 0.001 mg to about 0.008 mg of Yohimbine HCl. The present invention, in a preferred dosage said diet supplement comprises about 0.0045 g of Yohimbine HCl per serving.

The aforementioned ingredients in embodiments of the present invention, are combined to form several embodiments. Specific embodiments of the present invention are understood by the inventors to function in the capacity of a dietary supplement to aid in body fat loss, lipolysis while affording protection against reactive oxygen species resulting from the β-oxidation of fats are set forth below.

In one embodiment of the present invention, the composition includes a combination of one or more of the following, but not limited to an extract of green tea, Caffeine anhydrous, Deanol, and extract of *Aspidosperma quebracio-blanco*, yohimbine, an extract of *Cnidium monnieri*, an extract of *Evodia rutaecarpa* fruit and Inositol Hexaphosphate. The composition of the present invention is in the nature of a dietary supplement wherein the dietary supplement may be consumed by an individual in any acceptable form. For example, the dosage form of the supplement may be provided as, e.g., a powder beverage mix, a liquid beverage, a ready-to-eat bar or drink product, a capsule, a tablet, a caplet, a liquid caplet, or as a dietary gel. The most preferred mode of delivery of the present embodiment is that of a liquid capsule.

In a second embodiment of the present invention, the composition includes a combination of one or more of the following, but not limited to an extract of green tea, caffeine anhydrous, and extract of black tea, an extract of oolong tea, an extract of red tea (rooibos tea), and extract of white tea, vinpocetne, *Coleus foskohlii*, cocoa seed and an extract of *Evodia rutaecarpa*. The composition of the present invention is in the nature of a dietary supplement, wherein the dietary supplement may be consumed in any acceptable form. For example, the dosage form of the supplement may be provided as, e.g., a powder beverage mix, a liquid beverage, a ready-to-eat bar or drink product, a capsule, a tablet, a caplet, a liquid caplet, or as a dietary gel. The most preferred mode of delivery of the present invention is that of a liquid capsule.

In a third embodiment of the present invention comprises a combination of one or more of an extract of green tea, caffeine anhydrous, and extract of *Cissus quadrangularis*, niacin, and extract of white willow bark, and extract of black pepper. The composition of the present invention is in the nature of a dietary supplement, wherein the dietary supplement may be consumed in any acceptable form. For example, the dosage form of the supplement may be provided as, e.g., a powder beverage mix, a liquid beverage, a ready-to-eat bar or drink product, a capsule, a tablet, a caplet, a liquid caplet, or as a dietary gel. The most preferred mode of delivery of the present embodiment is that of a liquid capsule.

Furthermore, the dosage form of the dietary supplement composition of embodiments of the present invention may be provided in accordance with any of the known customary processing techniques for herbal and/or dietary supplements in any of the aforementioned forms.

In an compositional example embodiment of the present invention, which is set forth in greater detail in Example 1, a dietary supplement comprised of green tea dry leaf extract (*Camellia sinensis*), anhydrous caffeine, *Cissus quadrangularis* extract, deanol, xanthinol nicotinate, inositol hexaphosphate, troxerutin (as *Sophora japonica*), *Evodia rutaecarpa* extract (*Teradium ruticarpum*), *Inula racemosa* extract (from root), *Cnidium monnieri* extract (seed), black pepper extract (*Piper nigrum* L), yohimbine hydrochloride (methyl 17-alpha-hydroxy-yohimban-16 alpha-carboxylate hydrochloride), *Aspidosperma quebracho-blanco* extract (bark), *Codonopsis pilosula* extract (root), and white willow bark extract (*Salix alba*) is provided for increasing individual's natural adipose lipolytic metabolism via adipose metabolism by way of lipolysis or lipolytic metabolism, and thermogenic means while simultaneously affording protection to the body of individual from reactive oxygen species resulting from the β-oxidation of fats and inhibiting the reformation of triglycerides in the body.

In a second compositional example embodiment of the present invention, which is set forth in greater detail in Example 2, is a dietary supplement comprised of green tea dry leaf extract (*Camellia sinensis*), anhydrous caffeine, banaba leaf extract (*Lagerstroemia speciosa* L.), black tea leaf extract (*Camellia sinensis* L.), about white tea leaf extract (*Camellia sinensis*), oolong tea dry leaf extract (*Camellia sinensis*), rooibos tea extract (*Aspalathus linearis*), vinpocetine, *Coleus forskholli* extract, *Theobroma cacao* extract (from seed), and *Evodia rutaecarpa* fruit extract (*Tetradium ruticarpum*) is provided for increasing individual's natural adipose lipolytic metabolism via adipose metabolism by way of lipolysis or lipolytic metabolism, and thermogenic means while simultaneously affording protection to the body of individual from reactive oxygen species resulting from the β-oxidation of fats and inhibiting the reformation of triglycerides in the body.

A third compositional example embodiment of the present invention, which is set forth in greater detail in Example 3, is a dietary supplement comprised of anhydrous caffeine, green tea dry leaf extract, *Cissus quadrangularis* extract (from stem and leaves), (*Camellia sinensis*), soy albumin bean extract powder, vitamin B-6 (pyridoxine hydrochloride), picamilon HCl, L-selenomethionine, Niacin, vitamin B-12 (cyanocobalamin), chromium polynicotinate, white pepper powder, oolong tea dry leaf extract (*Camellia sinensis*), quercetin dihyrdrate (citrus bioflavanoid), white willow bark extract (*Salix alba*), rooibos tea extract (*Aspalathus linearis*), black tea leaf extract (*Camellia sinensis* L.), and folic acid is provided for increasing individual's natural adipose lipolytic metabolism via adipose metabolism by way of lipolysis or lipolytic metabolism, and thermogenic means while simultaneously affording protection to the body of individual from reactive oxygen species resulting from the β-oxidation of fats and inhibiting the reformation of triglycerides in the body.

The present invention may be utilized for increasing an individual's natural adipose metabolism by way of lipolysis or lipolytic metabolism, thus leading to a desired body fat composition while promoting stored energy utilization manifesting in thermogenesis in an individual and simultaneously affording protection to the body of individual from reactive oxygen species resulting from the β-oxidation of fats while inhibiting the reformation of triglycerides in the body. The compositions of the present invention are of particular interest and advantageous to those seeking to lose body fat mass, such as bodybuilders and athletes or those suffering from excess body fat. The amount of the composition administered to the athlete and/or person is variable dependant upon the desired effect, body mass, and the individual characteristics of the athletes and/or persons as well as the like. For example, in various embodiments, the subject compositions are administered to the diet of the athlete and/or bodybuilder and/or person on a daily basis.

In addition to compositions, the present invention also provides various methods of increasing an individual's natural adipose burning metabolism lipolysis or lipolytic metabolism, thus leading to a desired body fat composition while promoting stored energy utilization manifesting in thermogenesis in an individual and simultaneously affording protection to the body of individual from reactive oxygen species resulting from the β-oxidation of fats while inhibiting the reformation of triglycerides in the body. Preferably, the method of the present invention provides a manner of consuming a composition of the present invention in the form of a dietary supplement. According to at least one embodiment of the present invention, the method provides for the consumption of a composition that reduces body fat mass leading to change in body mass composition according to the aforementioned parameters. For example, the consumption of the composition in accordance with the method will allow an individual's body to burn more stored body fat than they would otherwise burn, leading to hardcore fat loss.

As aforementioned, the diet supplement compositions according to the present invention may be employed in methods for increasing an individual's natural adipose metabolism. The methods of the present invention are of particular interest and advantageous to those seeking to lose body fat mass, such as hardcore bodybuilders and/or athletes or those suffering from an elevated body mass. The methods may involve a determination, and an administration of an amount of a composition in accordance with factors such as the desired effect, the body weight and the characteristics of the athlete and/or bodybuilder and/or person and the like. For example, in preferred embodiments, the method includes the administration of the aforementioned compositions to the diet of the athlete and/or bodybuilder and/or person on a daily basis.

Although the following examples illustrate the practice of the present invention according to various embodiments thereof, the examples should not be construed as limiting the scope of the invention. Other embodiments of the present invention will be apparent to those skilled in the art from consideration of the specification and examples.

Example 1

A dietary supplement comprising the following ingredients per serving is prepared for consumption as a caplet: about 0.46 g of green tea dry leaf extract (*Camellia sinensis*) which is standardized for 90% polyphenols, 75% catechins, 45% epigallocatechin gallate, about 0.3 g of anhydrous caffeine, about 0.15 g of *Cissus quadrangularis* extract (from stem and leaves) which is standardized for 2.5% phytosterols, about 0.1 g of deanol bitartrate, about 0.05 g of xanthinol nicotinate, about 0.02 g of inositol hexaphosphate, about 0.02 g of troxerutin (as *Sophora japonica*) which is standardized for 97% trihydroxyethylrutoside, about 0.01 g of *Evodia rutaecarpa* extract (*Teradium ruticarpum*) from fruit which is standardized for 10% evodiamine, about 0.01 g of *Inula racemosa* extract (from root) which is standardized for 2% alantolactone, about 0.01 g of *Cnidium monnieri* extract (seed) which is standardized for 20% osthole, about 0.005 g of black pepper extract (*Piper nigrum* L) from fruit which is standardized for 95% piperine, about 0.0045 g of yohimbine hydrochloride (methyl 17-alpha-hydroxy-yohimban-16 alpha-carboxylate hydrochloride), about 0.001 g of *Aspidosperma quebracho-blanco* extract (bark) which is standardized for 0.3% alkaloids, about 0.001 g of *Codonopsis pilosula* extract (root), and about 0.001 g of white willow bark extract (*Salix alba*) which is standardized for 25% salicin.

Preferably, the nutritional composition is consumed in accordance with the following directions:

Directions: As a dietary supplement, take 3 capsules with an 8 oz. glass of water 2 times daily, approximately 30 to 60 minutes before meals. On days of wherein the individual undertakes a physical workout, take 1 of aforementioned servings before the workout.

Example 2

A dietary supplement comprising the following ingredients per serving is prepared for consumption as a tablet:
about 0.2 g of green tea dry leaf extract (*Camellia sinensis*) which is standardized for 90% polyphenols, 75% catechins, 45% epigallocatechin gallate, about 0.2 g of anhydrous caffeine, about 0.024 g of banaba leaf extract (*Lagerstroemia speciosa* L.) which is standardized for 3% corosolic acid, about 0.001 g of black tea leaf extract (*Camellia sinensis* L.) which is standardized for 70% polyphenols, 50% catechins, 25% epigallocatechin gallate, about 0.001 g of white tea leaf extract (*Camellia sinensis*) which is standardized for 50% polyphenols, 35% catechins, 15% epigallocatechin gallate, about 0.001 g of oolong tea dry leaf extract (*Camellia sinensis*) which is standardized for 50% polyphenols, 25% catechins, 15% epigallocatechin gallate, about 0.001 g of rooibos tea extract (*Aspalathus linearis*) from leaf and stem which is standardized for 20% polyphenols, about 0.001 g of vinpocetine, about 0.001 g of *Coleus forskholli* extract (from root) which is standardized for 10% forskolin, about 0.001 g of *Theobroma cacao* extract (from seed) which is standardized for 6% theobromine, and about 0.001 g of *Evodia rutaecarpa* fruit extract (*Tetradium ruticarpum*) which is standardized for 10% evodiamine.

Preferably, the nutritional composition is consumed in accordance with the following directions:
Directions: As a dietary supplement, take 2 capsules with an 8 oz. glass of water, 2 times daily. On days of wherein the individual undertakes a physical workout, take 1 of aforementioned servings before the workout.

Example 3

A dietary supplement comprising the following ingredients per serving is prepared for consumption as a liquid gel capsule:
about 0.25 g of anhydrous caffeine, about 0.15 g of *Cissus quadrangularis* extract (from stem and leaves) which is standardized for 2.5% phytosterols, about 0.1222 g of green tea dry leaf extract (*Camellia sinensis*) which is standardized for 90% polyphenols, 45% epigallocatechin gallate, about 0.05 g of soy albumin bean extract powder (glycine max), about 0.05 g of vitamin B-6 (pyridoxine hydrochloride), about 0.05 g of picamilon HCl, about 0.012 g of L-selenomethionine, about 0.005 g of Niacin, about 0.005 g of vitamin B-12 (cyanocobalamin), about 0.015 g of chromium polynicotinate, about 0.001 g of white pepper powder, about 0.001 g of oolong tea dry leaf extract (*Camellia sinensis*) which is standardized for 50% polyphenols, 25% catechins, 15% epigallocatechin gallate, about 0.001 g of quercetin dihyrdrate granular (citrus bioflavanoid), about 0.001 g of white willow bark extract (*Salix alba*) which is standardized for 25% salicin, about 0.001 g of rooibos tea extract (*Aspalathus linearis*) from leaf and stem which is standardized for 20% polyphenols, about 0.001 g of black tea leaf extract (*Camellia sinensis* L.) which is standardized for 70% polyphenols, 50% catechins, 25% epigallocatechin gallate, and about 0.0004 g of folic acid.

Preferably, the nutritional composition is consumed in accordance with the following directions:
Directions: As a dietary supplement, take 2 liquid gel capsules with a glass of water 2 times daily, before meals. For best results; use for 8 weeks in conjunction with a sensible diet and a regular exercise program. On days of wherein the individual undertakes a physical workout, take 1 of aforementioned servings before the workout.

EXTENSIONS AND ALTERNATIVES

In the foregoing specification, the invention has been described with specific embodiments thereof, however, it will be evident that various modifications and changes may be made thereto without departing from the broader spirit and scope of the invention.

What is claimed is:

1. A method to aid in bodily fat loss of an individual, the method comprising the step of:
administering to the individual in need thereof an effective amount of a composition comprising:
one or more lipolytic substances;
one or more thermogenic substances; and
an extract of *Sophora japonica* standardized for 97% troxerutin.

2. The method of claim 1, wherein said composition further comprising a substance to inhibit reformation of triglycerides in the bodily tissues of an individual.

3. The method of claim 1, wherein said lipolytic substance is selected from the group consisting of an extract of green tea, caffeine anhydrous, an extract of *Evodia rutaecarpa*, deanol, and yohimbine.

4. The method of claim 1, wherein the thermogenic substance is selected from the group consisting of an extract of green tea, caffeine anhydrous, and deanol.

5. The method of claim 2, wherein the substance to inhibit the reformation of triglycerides is an extract of black pepper (*Piper nigrum*).

6. The method of claim 1, wherein said composition additionally contains at least one antioxidant selected from the group consisting of green tea polyphenols, an extract of black pepper (*Piper nigrum*), *Cissus quadrangularis*, and inositol hexaphosphate.

7. The method of claim 1, wherein the composition additionally comprises at least one element selected from the group consisting of xanthinol nicotinate, *Inula racemosa* extract, *Cnidium monnieri* extract, *Aspidosperma quebracho-blanco* extract, *Codonopsis pilosula* extract, soybean albumin extract powder, vitamin B-6, picamilon HCl, L-selenomethionine, niacin, vitamin B-12, chromium polynicotinate, white pepper powder, quercetin dihydrate, rooibos tea extract, folic acid, banaba leaf extract, vinpocetine, *Coleus forskohlii*, cocoa seed and white willow bark extract.

8. The method of claim 1, wherein the composition is in the form of a powder beverage mix, a liquid beverage, a ready-to-eat bar or drink product, a capsule, a tablet, a caplet, a liquid caplet, a dietary gel or a liquid capsule.

9. The method of claim 1, wherein the composition is administered before a meal.

10. The method of claim 1, wherein the composition is administered before a workout.

11. The method of claim 1, wherein the composition is administered over a course of about 8 weeks.

* * * * *